United States Patent
Myer et al.

(10) Patent No.: US 11,941,640 B2
(45) Date of Patent: Mar. 26, 2024

(54) ADAPTIVE RESPONSE TIMER SYSTEM AND METHOD

(71) Applicant: Quiq, Inc., Bozeman, MT (US)

(72) Inventors: Michael A. Myer, Bozeman, MT (US); Andrew Jenkins, Bozeman, MT (US)

(73) Assignee: Quiq, Inc., Bozeman, MT (US)

( * ) Notice: Subject to any disclaimer, the term of this patent is extended or adjusted under 35 U.S.C. 154(b) by 0 days.

(21) Appl. No.: 16/144,354

(22) Filed: Sep. 27, 2018

(65) Prior Publication Data
US 2019/0102781 A1 Apr. 4, 2019

Related U.S. Application Data

(60) Provisional application No. 62/565,959, filed on Sep. 29, 2017.

(51) Int. Cl.
  G06Q 30/016 (2023.01)
  G06Q 10/109 (2023.01)

(52) U.S. Cl.
  CPC ......... *G06Q 30/016* (2013.01); *G06Q 10/109* (2013.01)

(58) Field of Classification Search
  None
  See application file for complete search history.

(56) References Cited

U.S. PATENT DOCUMENTS

| | | | | |
|---|---|---|---|---|
| 10,447,853 | B1* | 10/2019 | Ouimette | H04M 3/5175 |
| 2010/0002863 | A1* | 1/2010 | Loftus | H04M 3/5158 |
| | | | | 379/265.02 |
| 2015/0256675 | A1* | 9/2015 | Sri | H04M 3/5183 |
| | | | | 379/265.09 |
| 2016/0036652 | A1* | 2/2016 | Bellini, III | G06F 9/44 |
| | | | | 709/223 |
| 2016/0261747 | A1* | 9/2016 | Thirugnanasundaram | |
| | | | | H04M 3/5232 |
| 2018/0219806 | A1* | 8/2018 | Girishankar | H04M 1/72436 |

OTHER PUBLICATIONS

Negash et al., Quality and effectiveness in web-based customer support systems Inf. Manag., 40 (8) (2003), pp. 757-768 (Year: 2003).*
Lemon, Katherine N., and Peter C. Verhoef. "Understanding customer experience throughout the customer journey." Journal of marketing 80.6 (2016): 69-96. (Year: 2016).*
Borowski, Craig, Are AI-Enabled Chatbots Ready for Customer Service?, Feb. 16, 2017, https://www.softwareadvice.com/resources/author/craigsoftwareadvice-com.
Borowski, Craig, "Customer Service Software Small Business Buyer Report—2014" Jul. 21, 2014, https://www.softwareadvice.com/resources/author/craigsoftwareadvice-com.

* cited by examiner

*Primary Examiner* — David P Sharvin
*Assistant Examiner* — Brock E Turk
(74) *Attorney, Agent, or Firm* — AVEK IP, LLC

(57) ABSTRACT

Prioritizing a customer service agent's responses to customer messages. In one form, an expected response time target is determined based on a time interval between sending an agent response and receiving a customer response from a particular customer. In other forms, other objective factors, such as message intervals, customer properties, and message properties, are used to determine the expected response time target. In yet other forms, a customer conversation can be automatically closed if the customer does not respond within a predetermined maximum time interval.

18 Claims, 6 Drawing Sheets

ADAPTIVE RESPONSE TIMER SYSTEM AND METHOD

CROSS-REFERENCE TO RELATED APPLICATIONS

This application claims priority to U.S. Provisional Patent Application Ser. No. 62/565,959, filed on Sep. 29, 2017, entitled "ADAPTIVE RESPONSE TIMER SYSTEM AND METHOD,", the entire disclosure of which is incorporated herein by reference.

FIELD

The present invention relates generally to customer service interactions via computing devices and communications networks and responding to customer inquiries through various communications channels.

BACKGROUND

Companies and businesses commonly utilize customer support systems in connection with their business in order to address customer issues. Historically, companies have used phone and emails as their customer support channels. However, the world has changed and people have demonstrated in the way that they communicate with friends and family that they prefer to use text messaging (SMS/text, Facebook Messenger, WhatsApp, iMessage, Kik, etc.) instead of making phone calls or sending email. As a result, companies and business have begun to utilize messaging features within their customer support operations in order to more actively engage with their customers. For example, the Quiq Messaging system, which operates as a Software as a Service (SaaS) application provided by Quiq, Inc., easily integrates with existing customer service systems to add messaging as a new communication channel for their customer support. With the Quiq Messaging system, customers can interact with the company via messaging, their preferred communication channel.

One issue that arises with the use of messaging as a customer support means is the expected level of engagement with customers. Specifically, when using messaging as a customer support means, companies need an effective means for determining how quickly to respond to customer requests issued through a messaging service and the appropriate sequences for responding to individual customer requests from a plurality of active customer requests. The present invention is directed to a system and method for automatically determining the appropriate response time to individual customer service requests through a messaging service in order to solve the aforementioned problems.

SUMMARY

In an aspect, systems and methods enable prioritizing a customer service agent's responses to customer messages by (i) receiving a first customer message from a customer computing device, the first customer message comprising a first customer service conversation between a customer and an agent, (ii) in response to receiving the first customer message, sending a first agent message to the first customer computing device, the first agent message further comprising the first customer service conversation, (iii) receiving a second customer message from the first customer computing device, the second customer message responding to the first agent message, and the second customer message further comprising the first customer service conversation, (iv) in response to receiving the second customer message, determining an expected response time target for responding to the second customer message, and (v) indicating, on an agent computing device, the expected response time target to the agent for prioritizing preparing a second agent message in response to said second customer message based on the expected response time target.

In another aspect, systems and methods enable prioritizing a customer service agent's responses to customer messages by (i) receiving a first customer message from a customer computing device, the first customer message comprising a first customer service conversation between a customer and an agent, (ii) in response to receiving the first customer message, adding the first customer service conversation to a schedule of one or more other customer service conversations for the agent, sending a first agent message to the first customer computing device and starting a timer, the first agent message further comprising the first customer service conversation, (iii) in response to the timer exceeding a predetermined maximum time interval without receiving a second customer message of the first customer service conversation, automatically removing the first customer service conversation from the schedule, and (iv) indicating, on an agent computing device, the removal of the first customer service conversation to the agent for prioritizing the one or more other customer service conversations.

BRIEF DESCRIPTION OF THE DRAWINGS

In the accompanying drawing, which forms a part of the specification and is to be read in conjunction therewith in which like reference numerals are used to indicate like or similar parts in the various views.

DETAILED DESCRIPTION

Figure 1:
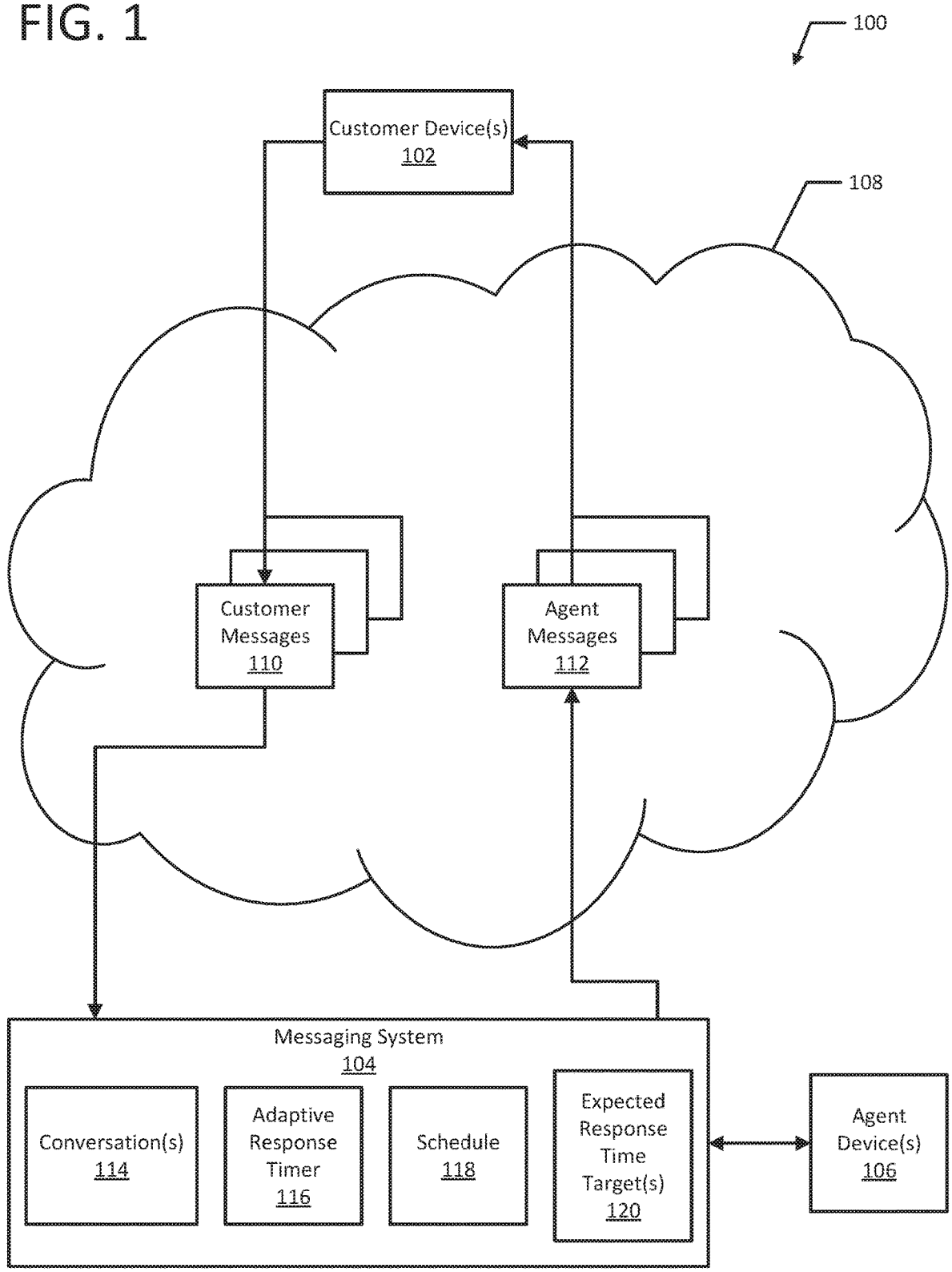
FIG. 1 is a schematic diagram of an adaptive response timer system and method in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

The present invention is directed toward an adaptive response timer (ART) system and method 100 for automatically determining an appropriate response time for responding to customer service inquiries during a customer service interaction and automatically prioritizing a customer service agent's responses to one or more customer service interactions. The ART system and method 100 of the present invention can be used in connection with any computerized system, service, application, or method used by companies to communicate with their customers via communications networks, such as, but not limited to the Quiq Messaging system, which is configured as a Software as a Service (Saas) application for customer service messaging.

Generally, the fundamentals of a positive interaction between two persons require that participants receive responses to their comments in a timeframe that meets their expectations. It is very frustrating to say something and not receive anything in response. The lack of response in most contexts indicates that the other party has left the conversation. For instance, if during a phone conversation, a first participant did not receive a response after having said something, the first participant would assume the other party was disconnected and would hang up the phone. However, in messaging, breaks in the conversation are entirely acceptable as participants are often messaging at the same time as another activity and will respond after they have finished the other activity. This could be minutes, hours, or sometimes days later. This concept can be referred to as Cadence and can differentiate between the two interaction styles as: (i) Synchronous—responses come at the same time, in response to a message (e.g., a phone call); and (ii) Asynchronous—responses are disjoint, occurring at an intermediate point in the future (e.g., text messaging).

Even though the Cadence of a conversation is Asynchronous, a societal norm has developed that guides the responsiveness of parties involved in a messaging conversation. If a second participant replies very quickly to a message sent by a first participant, there is an implied social obligation to respond quickly as well. In other cases, if the first participant sends a message and does not get a response right away, when the response arrives later, the same social obligation doesn't exist to respond quickly. In this delayed response case, the second participant is probably busy doing something else and they didn't have time to respond to the first participant right away. They also do not expect that the first participant will respond right away. This can be called the level of Engagement. If the second messaging participant is highly engaged (responsive) it would be rude if the first participant did not have a high level of engagement also (the first participant responds quickly). Participants in a conversation expect a similar level of engagement from the other party as their own level.

The number of simultaneous interactions is another way in which messaging can be different from other forms of communications channels. Because there are breaks in the conversation, (i.e., an asynchronous cadence), a participant can be involved in many messaging interactions at once since one interaction does not require full focus. This concept can be referred to as Concurrency. Historically, the primary communications channels through which customers have interacted with companies for customer service inquiries have been the traditional phone and email.

Table 1 illustrates the differences between the different types of communications channels that can be used by companies when engaging customers in customer service capacities. As shown, in addition to the traditional communications channels of phone and email, messaging can function as an alternative communications channel. The Cadence, Engagement Level, and Concurrency of the different communications channels varies due to the nature of the interaction between the participants of the conversation.

TABLE 1

| Channel | Cadence | Engagement Level | Concurrency |
| --- | --- | --- | --- |
| Phone | Synchronous | Always High - responses are expected immediately | Agents can process only one customer service conversation at a time |
| Email | Asynchronous | Low - responses are not expected immediately | Agents can process only one customer service conversation at a time |
| Messaging | Asynchronous | Variable - response time is dictated by societal norms that dictate agents mirror the level of engagement of the customer in the customer service conversation | Agents are able to process multiple customer service conversations at the same time |

As shown in Table 1, messaging is unlike any other communication channel because it has an asynchronous Cadence, variable Engagement Level, and high Concurrency. This can lead to a quandary for an agent handling many simultaneous conversations in a company's customer service contact center. The agent is now required to determine what ongoing customer service conversation should be addressed first, and the order in which the plurality of ongoing customer service conversations should be handled. If the agent chooses poorly, he or she may not respond in a timely manner (based on societal norms and the customer's expected response time) and upset the one or more customers who are expecting a higher level of engagement. This can result in a low level of customer satisfaction for the company and an unsatisfactory job rating for the agent.

The Adaptive Response Timer (ART) system and method 100 of the present invention can reduce the occurrence of untimely responses to customers in customer service conversations and prioritize for agents which conversation to respond to first and the appropriate time for responding by automatically keeping track of the variable level of engagement for each of the ongoing customer service conversations an agent is in charge of, calculating response time targets for each conversation based on the variable engagement level, and continuously prioritizing conversations for the agent, as described in greater detail below. In this manner, the ART system and method 100 described herein utilizes objective factors to prioritize communications with customers and thereby satisfy the customers' subjective expectations.

FIG. 1 provides a schematic representation of an exemplary embodiment of the ART system and method 100. As shown in FIG. 1, the ART system 100 includes one or more customer devices 102, a messaging system 104, and one or more agent devices 106. The customer devices 102 and the messaging system 104 are communicatively connected via a communications network 108 for sending and receiving customer messages 110 and agent messages 112. In the embodiment illustrated in FIG. 1, the messaging system 104 includes one or more conversations 114, an adaptive response timer (ART) 116, a schedule 118, and one or more expected response time targets 120.

Figure 2:
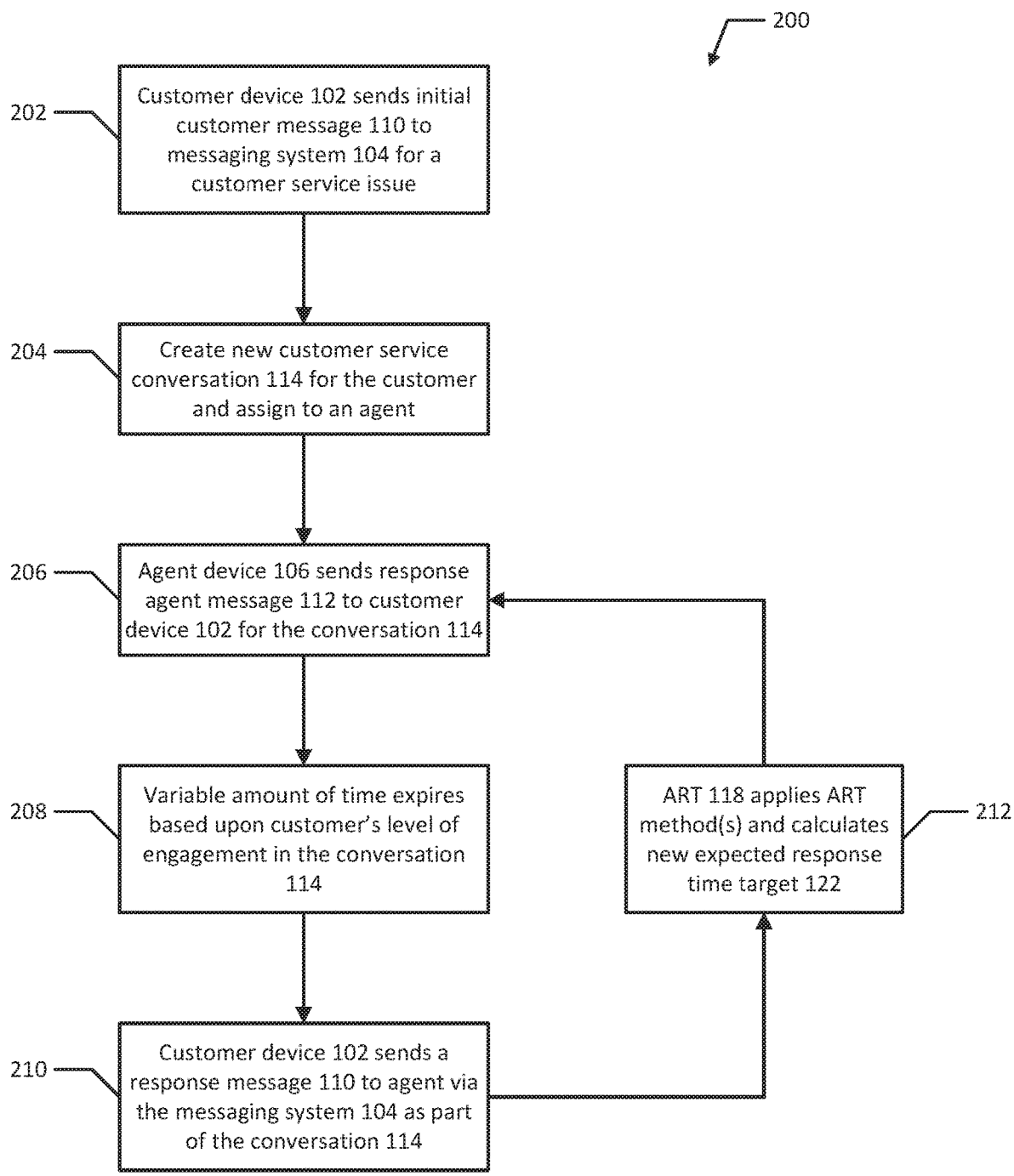
FIG. 2 is a schematic flowchart of one process component of an adaptive response timer system and method in accordance with one embodiment of the present invention.

FIG. 2 illustrates an exemplary response process 200 that can function as a sub-component of the ART system and method 100 of the present invention according to one embodiment. The exemplary response process 200 illustrated in FIG. 2 shows the steps for receiving and responding to an individual customer service conversation 114. As shown, at step 202, a customer device 102 sends an initial customer message 110 to the company via the messaging system 104 requesting service about a particular issue. For example, the message can be a text message (e.g., Short Message Service (SMS)), Facebook Messenger, WhatsApp, iMessage, Kik, or the like. In some embodiments, the customer device 102 can send the initial customer message 110 in response to an initial agent message 112. At step 204, a new customer service conversation 114 is created and logged for the customer and the new customer service conversation 114 is assigned to a particular agent. At step 206, the agent formulates a response agent message 112 to the customer for the customer service conversation 114 and the agent device 106 sends the response agent message 112 to the customer device 102. At step 208, a variable amount of time lapses before the customer device 102 sends a follow-up response customer message 110 for the customer service conversation 114 in step 210. The variable amount of time that lapses during step 208 establishes the customer's present level of engagement for the customer service conversation 114. The ART system and method 100 keeps track of the variable amount of time that lapses during step 208. At step 212, the ART system and method 100 (e.g., ART 116) calculates the expected response time target 120 based on the variable elapsed time and provides the expected response time target 120 to the agent. In an embodiment, the expected response time target 120 is calculated based at least in part on the customer's present level of engagement (e.g., a time interval between the response agent message 112 and the follow-up response customer message 110). The agent can then respond to the customer's message in the customer service conversation 114 in a manner consistent with the customer's expectations and/or the company's service level objectives and the process can be reiterated as illustrated in FIG. 2.

Additionally or alternatively, the expected response time target 120 can be calculated at step 212 based on other factors. Those skilled in the art will appreciate that the expected response time target 120 may calculated based on any combination of the factors described herein.

In an embodiment, the expected response time target 120 is calculated based at least in part on the level of engagement for conversations with the same current customer (e.g., customer device 102) that occurred prior to the current conversation 114. In another embodiment, the expected response time target 120 is calculated based at least in part on a status of the current customer. For example, if the customer is a "preferred" member or a "gold" customer or the like (e.g., based on the customer's rating criteria), then the ART system and method 100 can factor that status into the algorithm to reduce the calculated expected response time 120. In yet another embodiment, the expected response time target 120 is calculated based at least in part on an importance level of the current customer. For example, the importance level of the customer can be based upon the customer's purchase history, loyalty rating, shopping cart value, or the like. In another embodiment, the expected response time target 120 is calculated based at least in part on the level of engagement for prior conversations with other customers regarding the same or similar topics as the present conversation 114. In yet another embodiment, the expected response time target 120 is calculated based at least in part on the level of engagement for prior conversations with other customers that are similar to the current customer.

In another embodiment, the expected response time target 120 is calculated based at least in part on the emotion of the customer messages 110. For example, messages having all capital letters (i.e., screaming) may be indicative of customer anger. Thus, those messages indicative of customer anger may be given increased priority over messages indicative of a happy customer. An emotional context of the customer messages 110 may also be determined from emoticons/emojis within the messages. In some embodiments, machine learning and/or artificial intelligence (AI) techniques can be used to determine the emotional context of customer messages 110.

In yet another embodiment, the expected response time target 120 is calculated based at least in part on the origination of the conversation 114. For example, a prospective customer originating a conversation for a potential sale may be given increased priority over an existing customer originating a conversation for service issues.

In another embodiment, the expected response time target 120 is calculated based at least in part on the geolocation of the customer (e.g., customer device 102). For example, a customer located in New York City may expect a faster response than a customer located in the Midwest. Those skilled in the art will appreciate that the geolocation of customer devices 102 may be determined via Global Positioning System (GPS) techniques, pairings between an Internet Protocol (IP) address of the devices 102 and a geographical location, or the like. In yet another embodiment, the expected response time target 120 is calculated based at least in part on one or more demographic properties of the customer. For example, customers belonging to a certain generational demographic cohort (e.g., Millennials) may expect a faster response than customers belonging to other generational demographic cohorts.

In yet another embodiment, the expected response time target 120 is calculated based at least in part on whether the current conversation 114 is a follow-up from one or more prior conversations. For example, the current conversation 114 being a follow-up from a prior conversation may indicate that the issue from the prior conversation was not resolved to the customer's satisfaction. Thus, follow-up conversations may be given increased priority relative to original conversations. In another embodiment, the expected response time target 120 is calculated based at least in part on the length of the current conversation 114. For example, increases in the length of the conversation 114 (e.g., increase in time or number of messages) may indicate that the customer's patience is wearing thin. Thus, the lengthy conversation may be given increased priority relative to shorter conversations. In yet another embodiment, the current conversation 114 may be given increased priority when multiple customer messages 110 are received by the messaging system 104 before an agent responds with an agent message 112.

Figure 3:
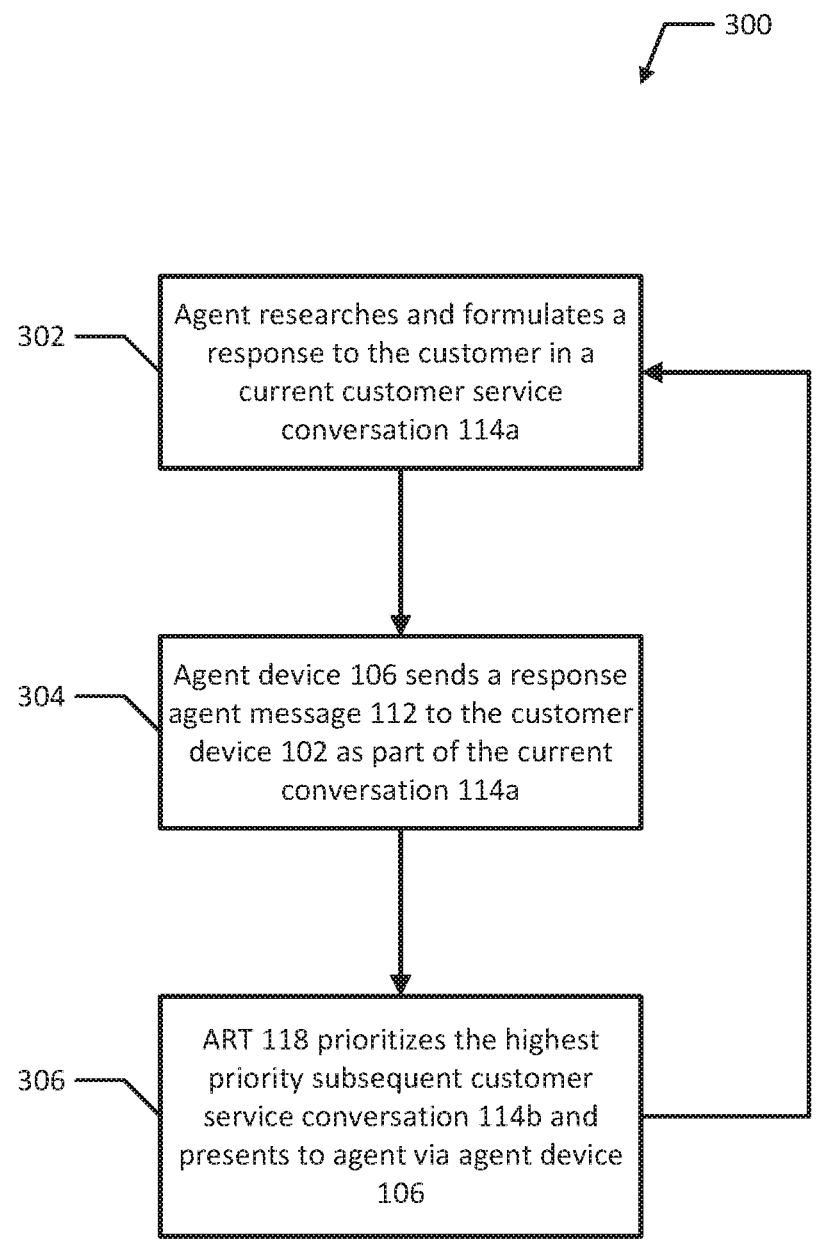
FIG. 3 is a schematic flowchart of another process component of an adaptive response timer system and method in accordance with one embodiment of the present invention.

FIG. 3 illustrates the continuous process 300 an agent can utilize in connection with the ART system and method 100 in order to timely respond to each of a plurality of customer service conversations 114 assigned to the agent according to one embodiment. As shown, at step 302, the agent prepares a response agent message 112 to the customer within a current customer service conversation 114a and then sends the response agent message 112 to the customer (e.g., customer device 102) at step 304. Then at step 306, the agent can select a subsequent customer service conversation 114b based on the highest priority conversation in the agent's assigned set of ongoing customer service conversations 114. As described in greater detail below, this prioritization of the ongoing customer service conversations 114 can be automatically completed by the ART system and method 100 and based, at least in part, on the customer's expected level of engagement in each ongoing customer service conversation.

Figure 4:
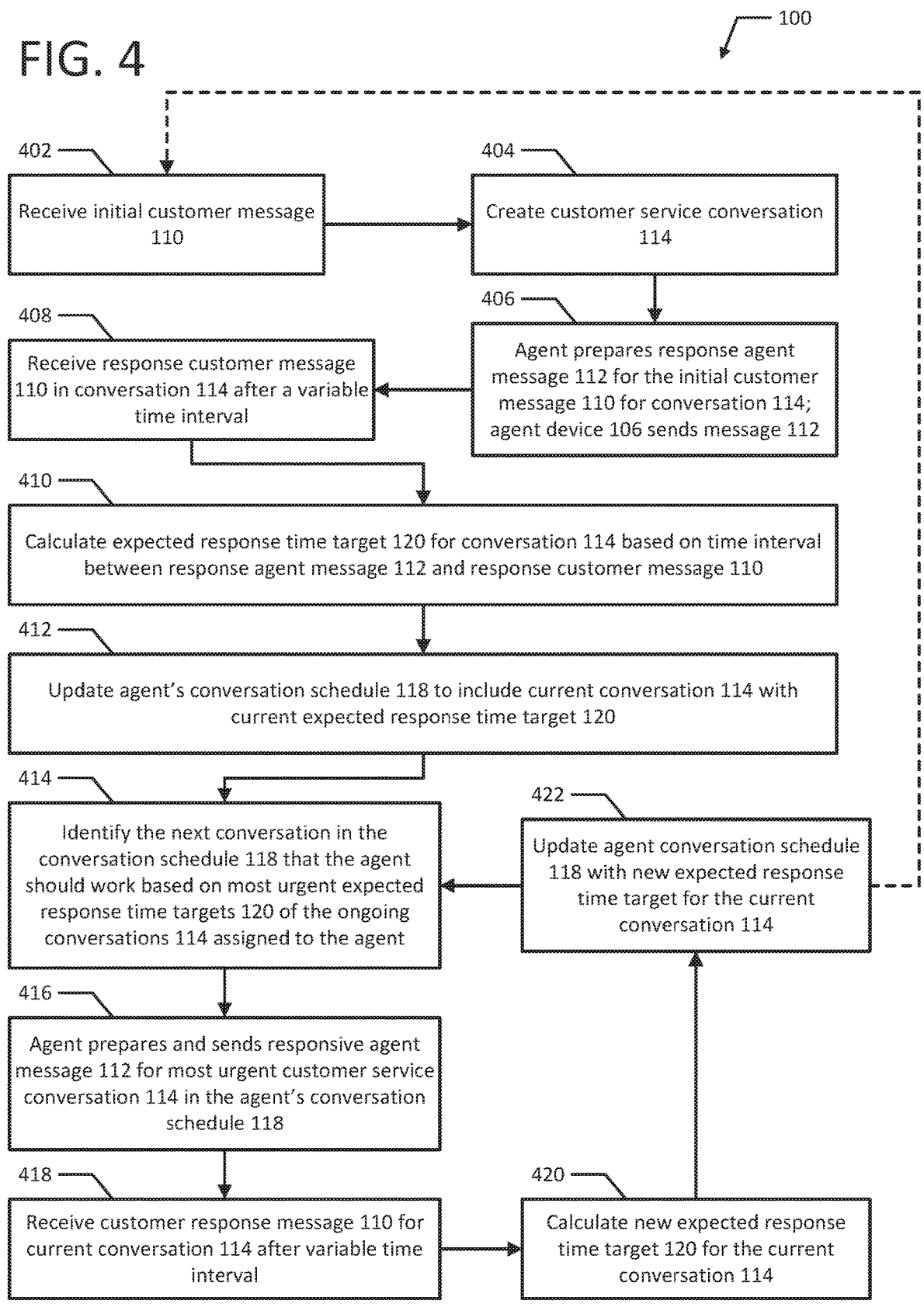
FIG. 4 is a schematic flowchart of an adaptive response timer system and method in accordance with one embodiment of the present invention.

FIG. 4 illustrates one embodiment of the process for the ART system and method 100 according to one embodiment of the present invention. As shown, the process can begin when a customer (e.g., customer device 102) sends an initial customer message 110 requesting customer service and it is received at the company's customer service control center (e.g., messaging system 104) at step 402. At step 404, a customer service conversation 114 is created for the received customer service request (from step 402) and it can be assigned a customer conversation identification number and then assigned to an agent for working the customer service request. At step 406, the agent can send a response agent message 112 for the customer service conversation 114 created at step 404. At step 408, after a variable amount of time has elapsed, the customer (e.g., customer device 102) may send a customer message 110 in response to the agent's initial message 112 as part of the customer service conversation 114. According to one embodiment, a maximum time interval can be established in the event of a non-response by a customer. For example, the customer service conversation 114 can be automatically closed and removed from the agent's schedule 118 if the customer (e.g., customer device 102) does not respond to an agent message 112 within the maximum time interval. The maximum time interval can be calculated based on any of the factors (e.g., those for calculating the expected response time target 120, etc.) described herein or any combination thereof.

Figure 5:
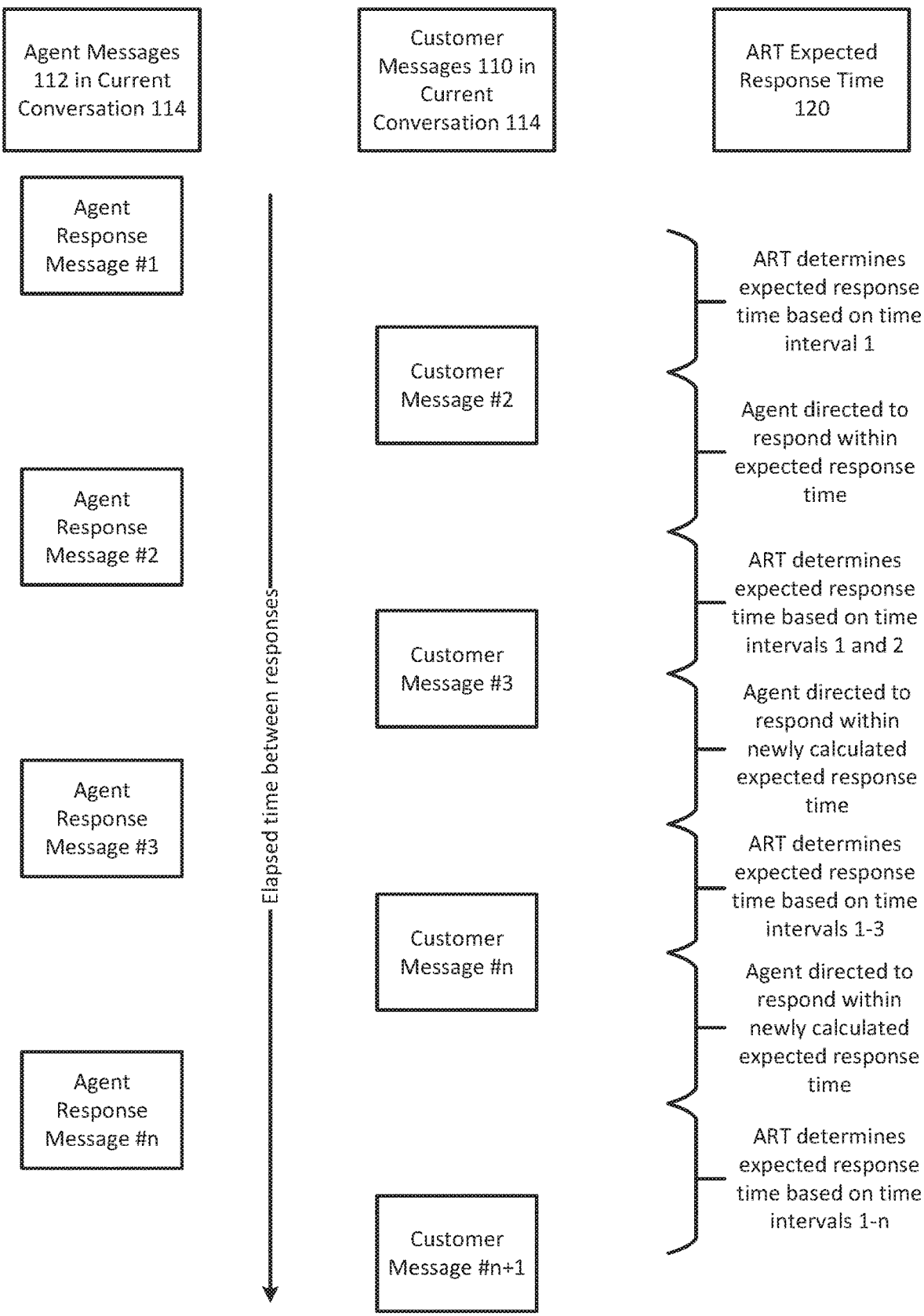
FIG. 5 is a schematic diagram of a customer service conversation analysis in connection with an adaptive response timer system and method in accordance with one embodiment of the present invention.

At step 410, the ART system and method 100 can calculate an expected response time target 120 for the customer service conversation 114 in order to establish a time period in which the agent should respond to the customer's initial response message 110. As also illustrated in FIG. 5, the expected response time target 120 can be calculated using an algorithm incorporated into the ART system and method 100 and can be based, at least in part, on the time interval that occurred between the agent's initial response message 112 and the customer's subsequent message 110 responding to the agent's message. This time interval can quantify the customer's level of engagement for the conversation and dictate the speed with which is expected for the agent to respond to result in a satisfactory customer experience during the customer service conversation 114. In other words, the time interval is an objective quantification of the customer's subjective expectations. Several additional factors can be incorporated into the expected response time algorithm, including general societal norms, and minimum and maximum response standards to supplement the elapsed time interval between the agent/customer messages. According to one embodiment, the ART algorithm can be configured to account for the status of the customer. For example, if the customer is a "preferred" member, or a "gold" customer, (based on the customer's rating criteria), then the ART system and method 100 can factor that into the algorithm to reduce the calculated expected response time 120. According to another embodiment, the ART algorithm can be configured to take into account the nature of the customer inquiry and adjust the expected response time 120 based on the relative "importance" of the inquiry. For example, if the customer inquiry is related to canceling the company's services, then ART system and method 100 could factor into the algorithm could the importance level of nature of the inquiry to adjust the calculated expected response time 120 based the importance of the nature of the inquiry. Both the status of the customer and the nature of the inquiry could be determined based upon thresholds set by an administrator. Those skilled in the art will appreciate that the expected response time target 120 may calculated based on any combination of the factors described herein. AI and machine learning techniques could also be incorporated into the algorithm to make determinations about the status of the customer and/or the nature of the customer inquiry.

Figure 6:
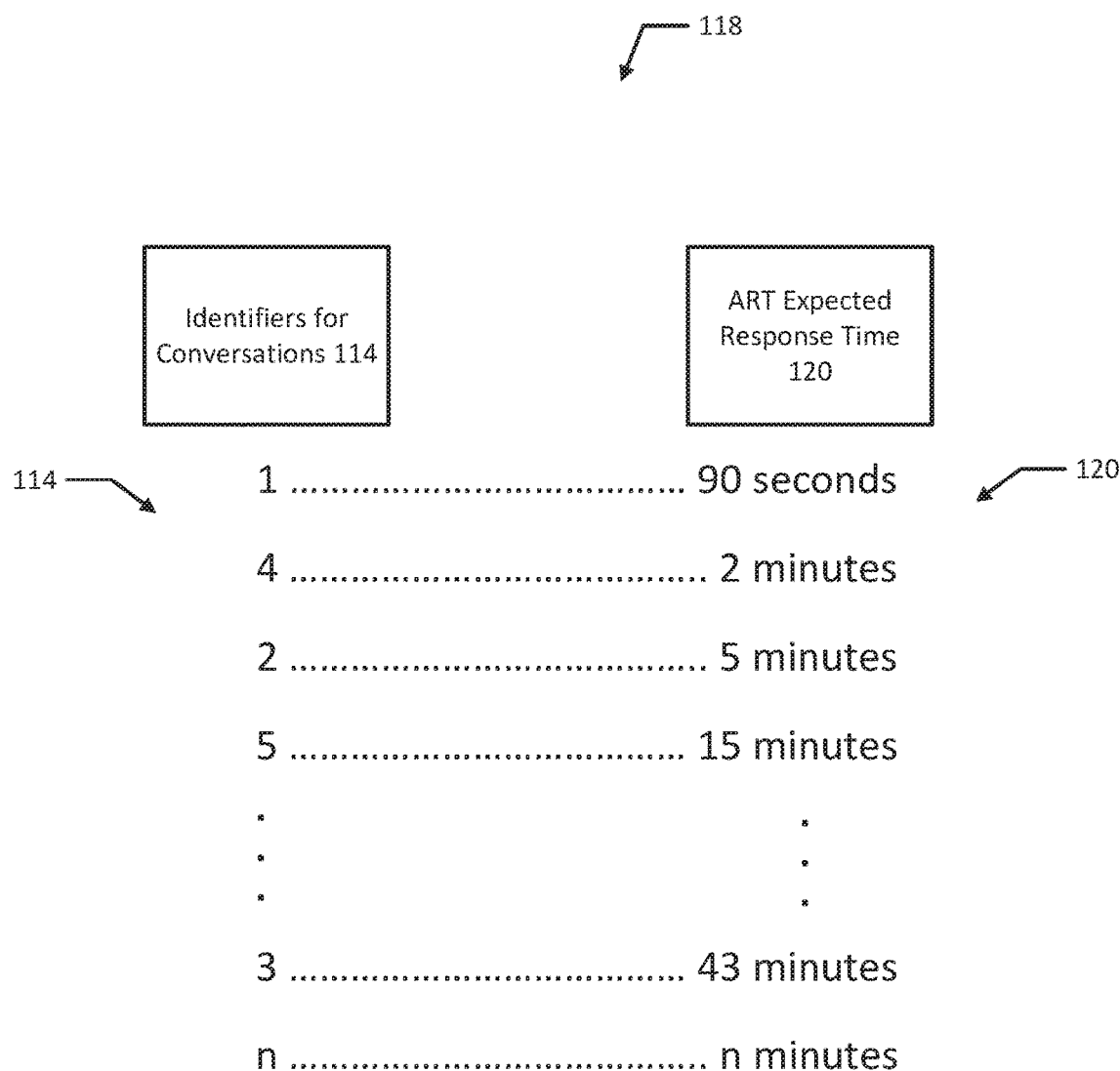
FIG. 6 is a schematic diagram of an agent conversation schedule for use in connection with an adaptive response timer system and method in accordance with one embodiment of the present invention.

Referring further to FIG. 4, at step 412, the ART system and method 100 can update the agent's conversation schedule 118 (also illustrated in FIG. 6 according to an exemplary embodiment). The agent's conversation schedule 118 can provide a list of the ongoing customer service conversations 114 (identified by their ID number, for example) assigned to the agent and the current expected response time target 120 for each conversation 114. When a new customer service conversation 114 is created and an initial expected response time target 120 is calculated during steps 402-410, each can be added to the agent's schedule 118 at step 412 to be included with the agent's current ongoing customer service conversations 114.

At step 414, the ART system and method 100 can indicate to the agent, which subsequent conversation 114 from the agent's ongoing conversations (as provided in the agent's schedule 118) should be selected for the agent to work on based on the most urgent expected response time targets 120 of the agent's ongoing conversations 114. At step 416, the agent can then prepare and send a responsive agent message 112 for the most urgent customer service conversation 114 selected by the ART system and method 100 at step 414 (and preferably within the expected response time target 120 for the selected conversation 114). At step 418, the customer may then send a response customer message 110 to the agent's most recent message 112 for the currently selected conversation 114 after a variable time interval.

At step 420, a new expected response time target 120 can be calculated using the response time algorithm incorporated into the ART system and method 100. As shown in more detail in FIG. 5, the new (or updated) expected response time target 120 can be based, at least in part, on the elapsed time interval between the most recent agent and customer messages (created between steps 416 and 418), the prior expected response time targets 120 for the conversation 114 (e.g., the previous time intervals between messages in the conversation 114), and/or other factors (such as societal norms, customer status, and nature of the customer inquiry, etc.) similar to those described herein. According to one embodiment, the response time algorithm utilized within the ART system and method 100 can be a weighted adaptive algorithm that can appropriately incorporate each of the previous time intervals between agent/customer message pairs and/or predict the time interval of the next response. In another embodiment, the algorithm can only take into account the most recent time interval between the agent and customer messages. Several other configurations of the response time algorithm can also be incorporated into the ART system and method 100 in certain embodiments of the present invention.

At step 422, the agent's conversation schedule 118 can then be updated to reflect the new/updated expected response time target 120 for the particular conversation 114. The process for the ART system and method 100 can then proceed back to step 414, where the agent can be prompted to work on the most urgent conversation 114 in the agent's updated conversation schedule 118. According to certain embodiments, as also shown in FIG. 4, if a new initial customer message 110 is received by the company and assigned to the agent, the process can revert back to the initial steps 402-412 to create and respond to the new customer service conversation 114, and update the agent's schedule 118 with the new conversation 114 before proceeding back to step 414. In addition, in certain embodiments, at various points along the process established by the ART system and method 100, the process can be designed to check to see whether an ongoing customer service conversation 114 has been fully addressed by the agent and/or whether the customer has disengaged a conversation 114, and that conversation 114 can be removed from the agent's schedule.

FIG. 5 provides a schematic representation of how the expected response time target 120 can be calculated by the ART algorithm of the ART system and method 100. As shown, according to certain embodiments of the present invention, the expected response time target 120 (which can represent the level of engagement of the customer for the particular customer service conversation) can be calculated using the elapsed time interval of the most recent agent/customer messages 112, 110 in the current conversation 114 and/or the prior time intervals between agent/customer message pairs in the current conversation 114. In addition, as also illustrated in FIG. 5, the expected response time target 120 for a particular conversation 114 can be updated after each round of agent/customer messages in order to reflect the most current level of engagement of the customer for the conversation 114 in certain embodiments of the present invention. In addition, as described above, other factors can be included in the algorithm for determining the expected response time target 120, such as customer status and the nature of the customer inquiry (i.e., importance levels).

FIG. 6 provides a schematic representation of an agent conversation schedule 118 that can be used in the ART system and method 100 of the present invention. As shown, the schedule 118 can include each of the ongoing customer service conversations 114 assigned to the agent and the current expected response time target 120 for each conversation 114. This schedule 118 (as described above) can dictate which conversation 114 the agent should select to work subsequent a completed response message.

The ART system and method 100 can be incorporated into a computer and/or software-based system or network in various embodiments of the present invention. For example, the ART system and method 100 of the present invention can comprise a computer system with one or more computers, databases and networks configured to send, receive and store messages received by customers for customer service requests. The system can further include one or more processors and programming instructions to create/assign conversations 114 for the received customer messages 110, allow the agent to send response messages 112 and to create, store, and update one or more agent's conversation schedules 118. In addition, the system can be configured to use one or more algorithms for automatically calculating the expected response time targets 120 for the customer service conversations 114 and storing (e.g., in one or more memory devices) the targets 120 in connection with the schedules 118 of each agent. It is also recognized that several other additional or alternative components can be incorporated into the ART system and method 100 in various embodiments of the present invention.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A computer-implemented method for prioritizing a customer service agent's responses to customer messages in an adaptive response timer system, said method comprising:
receiving, by a processor of a messaging system, a customer message from a customer computing device;
sending, by the processor, the customer message to an agent computing device, the customer message comprising a current customer service conversation;
receiving, by the processor, an agent message from the agent computing device;
sending, by the processor, the agent message to the customer computing device, the agent message further comprising the current customer service conversation;
receiving, by the processor from the customer computing device, a subsequent customer message, the subsequent customer message responding to the agent message, and the subsequent customer message further comprising the current customer service conversation;
sending, by the processor, the subsequent customer message to the agent computing device;
tracking, by the processor, a duration of time between the sending the agent message to the customer and the receiving the subsequent customer message from the customer;
determining, by the processor, a level of engagement of the customer based on the duration of time by the messaging system;
calculating, by the processor, an expected response time target for responding to the subsequent customer message based on the level of engagement, wherein the greater the level of engagement the shorter expected response time target;

adding, by the processor, the subsequent customer message to an agent conversations schedule, wherein the agent conversations schedule includes ongoing customer service conversations assigned to the agent, and wherein the ongoing customer conversations include expected response time targets calculated for each of the ongoing customer conversations;

determining, by the processor, that the customer has disengaged with the current customer service conversations;

removing, by the processor, the current customer service conversation from the agent conversations schedule;

creating, by the processor, a prioritized listing of the ongoing customer service conversations based on expected response time targets of the ongoing customer conversations;

presenting, by the processor, the prioritized listing to the agent computing device;

identifying, by the processor, a next conversation in the agent conversations schedule selected from a top of the prioritized listing;

calculating, by the processor, a new expected response time target for the next conversation; and updating, by the processor, the agent conversations schedule with the new expected response time target for the next conversation.

2. The computer-implemented method of claim 1, wherein said calculating the expected response time target for responding to the subsequent customer message is further based on one or more time intervals between one or more previous messages between the customer and the agent during one or more other customer service conversations, the one or more other customer service conversations occurring before the current customer service conversation.

3. The computer-implemented method of claim 1, wherein said calculating the expected response time target for responding to the subsequent customer message is further based on a status of the customer.

4. The computer-implemented method of claim 1, wherein said calculating the expected response time target for responding to the subsequent customer message is further based on an importance level of the customer.

5. The computer-implemented method of claim 1, wherein said calculating the expected response time target for responding to the subsequent customer message is further based on one or more time intervals between one or more previous messages between one or more other customers and the agent or one or more other agents, the one or more previous messages having topics similar to a topic of a first customer service conversation.

6. The computer-implemented method of claim 1, wherein said calculating the expected response time target for responding to the subsequent customer message is further based on one or more time intervals between one or more previous messages between one or more other customers and the agent or one or more other agents, wherein the customer is similar to the one or more other customers.

7. The computer-implemented method of claim 1, wherein said calculating the expected response time target for responding to the subsequent customer message is further based on receiving a plurality of customer messages before sending the agent message.

8. The computer-implemented method of claim 1, wherein said calculating the expected response time target for responding to the subsequent customer message is further based on an emotional context of the customer message.

9. The computer-implemented method of claim 1, wherein said calculating the expected response time target for responding to the subsequent customer message is further based on an origin of the customer message.

10. The computer-implemented method of claim 1, wherein said calculating the expected response time target for responding to the subsequent customer message is further based on a geolocation of the customer computing device.

11. The computer-implemented method of claim 1, wherein said calculating the expected response time target for responding to the subsequent customer message is further based on a demographic of the customer.

12. The computer-implemented method of claim 1, wherein said calculating the expected response time target for responding to the subsequent customer message is further based on a follow-up status of the customer message.

13. The computer-implemented method of claim 1, wherein said calculating the expected response time target for responding to the subsequent customer message is further based on a length of the customer service conversation.

14. The computer-implemented method of claim 1, wherein determining the customer has disengaged with the customer service conversation comprises:

determining, by the processor, that a time interval without receiving the subsequent customer message of the customer service conversation exceeds a predetermined maximum time interval; and determining, by the processor, that the ongoing conversation has been considered by the agent.

15. The computer-implemented method of claim 14, wherein the predetermined maximum time interval is based on at least one of:

one or more time intervals between one or more previous messages between the customer and the agent during one or more other customer service conversations, the one or more other customer service conversations occurring before the customer service conversation;

one or more time intervals between one or more previous messages between one or more other customers and the agent or one or more other agents, the one or more previous messages having topics similar to a topic of the customer service conversation;

one or more time intervals between one or more previous messages between one or more other customers and the agent or one or more other agents, wherein the customer is similar to the one or more other customers; and receiving, by the processor, a plurality of customer messages before sending an agent message.

16. The computer-implemented method of claim 14, wherein the predetermined maximum time interval is based on at least one of:

a status of the customer;

an importance level of the customer; and a demographic of the customer.

17. The computer-implemented method of claim 14, wherein the predetermined maximum time interval is based on at least one of:

an emotional context of the customer message;

an origin of the customer message;

a follow-up status of the customer message; and a length of the customer service conversation.

18. The computer-implemented method of claim 14, wherein the predetermined maximum time interval is based on a geolocation of the customer computing device.

* * * * *